US011471390B2

(12) United States Patent
Park et al.

(10) Patent No.: US 11,471,390 B2
(45) Date of Patent: Oct. 18, 2022

(54) PSEUDOCERAMIDE COMPOUND AND USE THEREOF

(71) Applicant: DAEBONG LS, LTD, Incheon (KR)

(72) Inventors: Jin Oh Park, Seoul (KR); Ji Won Lee, Seoul (KR); Seong Hyeon Jeon, Suwon-si (KR); Jae Young Lee, Gunpo-si (KR); Hye Ja Lee, Seogwipo-si (KR); Bo Kyung Kwon, Gwangmyeong-si (KR)

(73) Assignee: DAEBONG LS, LTD, Incheon (KR)

( * ) Notice: Subject to any disclaimer, the term of this patent is extended or adjusted under 35 U.S.C. 154(b) by 159 days.

(21) Appl. No.: 16/755,727

(22) PCT Filed: Nov. 22, 2017

(86) PCT No.: PCT/KR2017/013381
§ 371 (c)(1),
(2) Date: Apr. 13, 2020

(87) PCT Pub. No.: WO2019/074158
PCT Pub. Date: Apr. 18, 2019

(65) Prior Publication Data
US 2020/0330350 A1 Oct. 22, 2020

(30) Foreign Application Priority Data
Oct. 11, 2017 (KR) .......................... 10-2017-0131556

(51) Int. Cl.
*A61K 8/42* (2006.01)
*A61Q 19/00* (2006.01)
*A61Q 19/02* (2006.01)
*C07C 231/02* (2006.01)
*C07C 233/20* (2006.01)

(52) U.S. Cl.
CPC ................ *A61K 8/42* (2013.01); *A61Q 19/00* (2013.01); *A61Q 19/007* (2013.01); *A61Q 19/02* (2013.01); *C07C 231/02* (2013.01); *C07C 233/20* (2013.01)

(58) Field of Classification Search
CPC ........... A61K 8/42; A61K 8/68; C07C 231/02
See application file for complete search history.

(56) References Cited

U.S. PATENT DOCUMENTS 6,410,597 B1 * 6/2002 Bieberich ............ A61K 31/045
514/738

FOREIGN PATENT DOCUMENTS

| KR | 10-0539965 B1 | 1/2006 |
| KR | 10-1750238 B1 | 6/2017 |
| KR | 10-2017-0076561 A | 7/2017 |

OTHER PUBLICATIONS

Fowler, C.J. et al. "Cyclooxygenation of the arachidonoyl side chain of 1-arachidonoylglycerol and related compounds block their ability to prevent anandamide and 2-oleoylglycerol metabolism by rat brain in vitro" Biochemical Pharmacology 69 (2005) 1241-1245 (Year: 2005).*
Tremblay, H. et al. "One-pot synthesis of polyunsaturated fatty acid amides with anti-proliferative properties" (Bioorganic & Medicinal Chemistry Letters 24 (2014) 5635-5638 (Year: 2014).*
Lipid Glossary (https://extension.okstate.edu/fact-sheets/lipid-glossary.html) available Dec. 2015, pp. 1-8 (Year: 2015).*
Tremblay, H. et al., "One-pot Synthesis of Polyunsaturated Fatty Acid Amides with Anti-proliferative Properties", Bioorganic & Medicinal Chemistry Letters, 2014, vol. 24, No. 24, pp. 5635-5638.
Couturier, L. et al., "Lipase-catalyzed Chemoselective Aminolysis of Various Aminoalcohols with Fatty Acids", Journal of Molecular Catalysis B: Enzymatic, 2009, vol. 56, pp. 29-33.
Fowler, C. J. et al., "Cyclooxygenation of the Arachidonoyl Side Chain of 1-arachidonoylglycerol and Related Compounds Block Their Ability to Prevent Anandamide and 2-oleoylglycerol Metabolism by Rat Brain in Vitro", Biochemical Pharmacology, 2005, vol. 69, pp. 1241-1245.

* cited by examiner

*Primary Examiner* — Andrew S Rosenthal
(74) *Attorney, Agent, or Firm* — Novick, Kim & Lee PLLC; Jae Youn Kim

(57) ABSTRACT

Provided are a novel pseudoceramide compound and uses thereof. The pseudoceramide has antioxidant, anti-inflammatory, skin whitening, and moisturizing effects. In addition, the pseudoceramide can be synthesized in a simple and economically advantageous manner and is free from problems associated with the preparation of cosmetic formulations resulting from low hydrophilicity, thus being suitable for use in cosmetic applications.

1 Claim, 5 Drawing Sheets

PSEUDOCERAMIDE COMPOUND AND USE THEREOF

TECHNICAL FIELD

The present invention relates to a novel pseudoceramide compound and uses thereof.

BACKGROUND ART

The skin functions to prevent moisture from escaping and to regulate our body temperature and fulfills sensory and immune functions in our body. Specifically, the stratum corneum of the skin serves as a protective barrier to external stimuli and foreign matter ingress. Healthy skin has a smooth and lustrous surface, is elastic, and gives a feeling of moistness. The inherent moisture content of the skin is the most important factor determining the texture of the skin. The elasticity and feelings of softness and moistness of the skin are maintained by the presence of moisture in the stratum corneum of the epidermis, the outermost layer of the skin. The moisture content of the stratum corneum is determined by sebaceous membrane, a lipid mixture produced from the epidermis, and by the natural moisturizing factor (NMR), a water-soluble component present in the stratum corneum. Moisture evaporation from the epidermis is described by the moisture retention function of ceramides found in intercellular lipids. It was reported that the stratum corneum loses its protective barrier function at a reduced concentration of ceramides in the skin, causing dermatological symptoms, for example, atopic dermatitis and psoriasis ((a) Fulmer amp; Kramer, J. Invest. Derm. 1986, 86, 598-602. (b) Tupker R. A. et al., Acta Derm. Venereol. Stockh, 1990, 70, 1-5.). Further, when the amount of ceramides is reduced, the skin tends to dry out and the skin surface loses its defense function, with the result that foreign matter easily enters the skin and secondary infections of the skin are caused, leading to skin rejection. Specifically, the entering matter causes cytokines to be released from keratinocytes, Langerhans cells, and melanocytes in the superficial dermis, resulting in infections. Accordingly, skin moisturization is important for the maintenance and improvement of skin barriers. Physiologic lipid mixtures including ceramide compounds were reported to accelerate the recovery of damaged skin barrier function compared to general moisturizers. Thus, there is a continuing need for such physiologic lipid mixtures. Particularly, several clinical tests revealed that physiologic lipid mixtures exhibit ameliorating effects on symptoms of patients with atopic dermatitis, similarly to medium- to high-potency external steroid preparations.

Since the importance of ceramides was widely recognized, many cosmetic and pharmaceutical companies have conducted research on the development of ceramide products. However, natural ceramides are difficult to extract and purify and they are economically disadvantageous. Thus, leading companies have made many efforts to develop pseudoceramides that are structurally similar to ceramides found in the skin and can produce functional effects identical to those of natural ceramides.

Some pseudoceramides have been developed by cosmetic companies in Korea, including Amorepacific Corp. (Korean Patent Publication No. 2017-0076561, "Patent Document 1") and Coreana Cosmetics Co., Ltd. (Korean Patent No. 10-0539965, "Patent Document 2"). The two patent documents are incorporated herein by reference in their entirety. However, difficulties in the preparation of the pseudoceramides incur considerable costs, limiting their general use. It is also known that currently commercially available natural ceramide compounds and pseudoceramide compounds have low hydrophilicity and solubility, making it difficult to provide products with high purity.

Therefore, there is a continuous need for research aimed at developing pseudoceramides with better physical properties that can be produced in a simple and economically advantageous manner.

PRIOR ART DOCUMENTS

Patent Documents (Patent Document 1) KR10-2017-0076561 A (Jul. 4, 2017)

(Patent Document 2) KR10-0539965 B1 (Jan. 10, 2006)

DETAILED DESCRIPTION OF THE INVENTION

Problems to be Solved by the Invention

The present invention intends to provide a novel synthetic pseudoceramide that can promote bioactivity to enhance the elasticity of the skin and exerts anti-inflammatory and whitening effects while avoiding the difficulties encountered in formulating natural ceramide compounds due to their economic problems and low hydrophilicity.

Means for Solving the Problems

The present invention has been made in an effort to solve the problems of the prior art and provides a pseudoceramide compound represented by Formula 1:

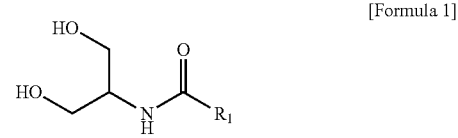

[Formula 1]

wherein $R_1$ is a carboxyl group-free $C_{13}$-$C_{21}$ unsaturated fatty acid residue.

The unsaturated fatty acid is myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid or docosahexaenoic acid.

The pseudoceramide compound may be represented by Formula 2:

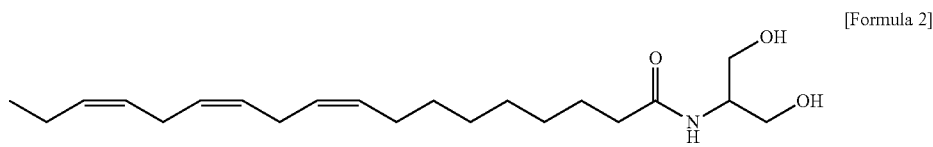 [SMILES: CC/C=C\C/C=C\C/C=C\CCCCCCCC(=O)NC(CO)CO]

[Formula 2]

The present invention also provides a method for preparing a pseudoceramide including reacting serinol represented by Formula 3:

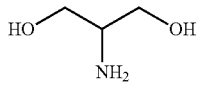
[Formula 3]

with an unsaturated fatty acid halide.

The present invention also provides an antioxidant cosmetic composition including the pseudoceramide compound as an active ingredient.

The present invention also provides an anti-inflammatory cosmetic composition including the pseudoceramide compound as an active ingredient.

The present invention also provides a skin whitening cosmetic composition including the pseudoceramide compound as an active ingredient.

The present invention also provides a skin moisturizing cosmetic composition including the pseudoceramide compound as an active ingredient.

Effects of the Invention

The pseudoceramide of the present invention has antioxidant, anti-inflammatory, skin whitening, and moisturizing effects. In addition, the pseudoceramide of the present invention can be synthesized in a simple and economically advantageous manner and is free from problems associated with the preparation of cosmetic formulations resulting from low hydrophilicity, thus being suitable for use in cosmetic applications.

BEST MODE FOR CARRYING OUT THE INVENTION

Figure 1:
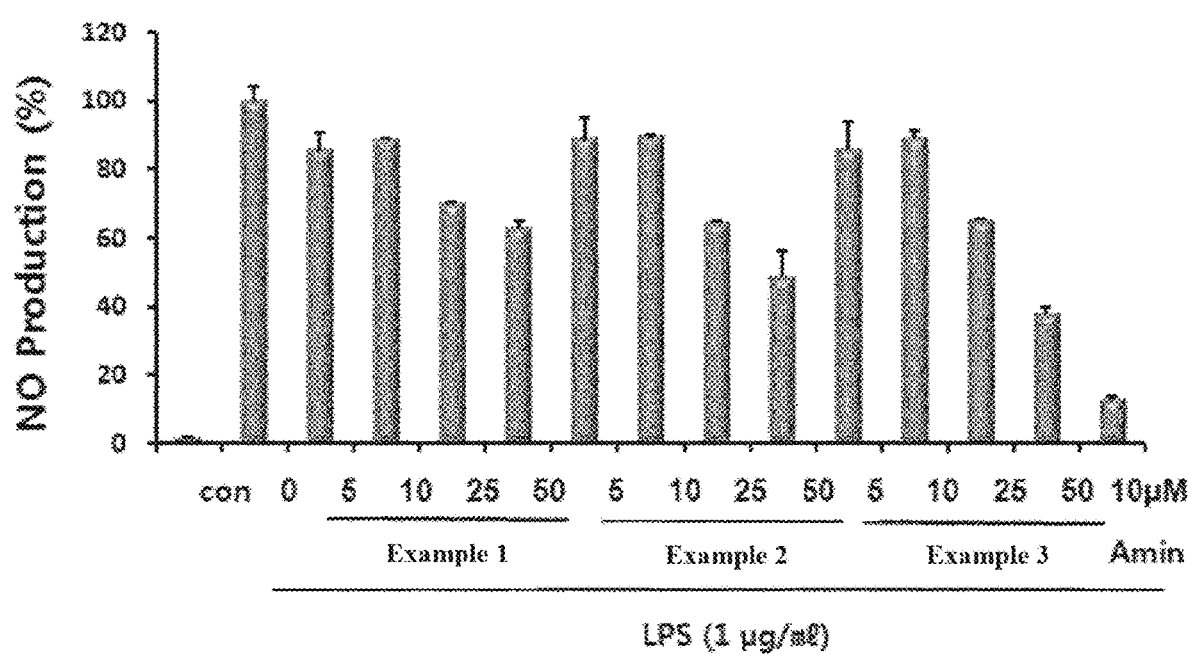
FIG. 1 is a graph showing the inhibitory activities of pseudoceramide compounds prepared in Examples 1-3 on nitric oxide (NO) production.

The present invention will now be described in detail.

One aspect of the present invention is directed to a pseudoceramide compound represented by Formula 1:

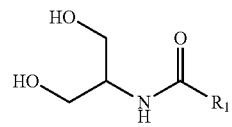
[Formula 1]

wherein $R_1$ is a carboxyl group-free $C_{13}$-$C_{21}$ unsaturated fatty acid residue.

The unsaturated fatty acid may be myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid or docosahexaenoic acid.

Particularly, the unsaturated fatty acid is α-linolenic acid. In this case, the pseudoceramide compound is represented by Formula 2:

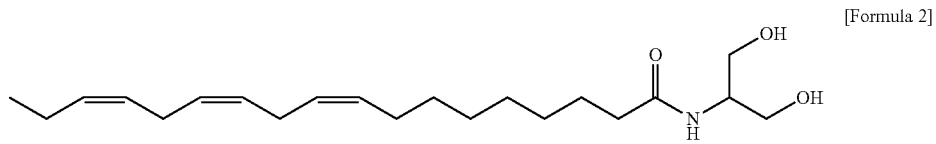
[Formula 2]

The compound of Formula 2 is more preferred for its better antioxidant, anti-inflammatory, and skin moisturizing effects than the compound containing any other unsaturated fatty acid residue, and further details thereof can be found in the Examples section that follows.

A further aspect of the present invention is directed to a method for preparing a pseudoceramide including reacting serinol (2-amino-1,3-propanediol, CAS No. 534-03-2) represented by Formula 3:

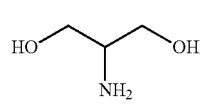
[Formula 3]

with an unsaturated fatty acid halide.

A basic design for the pseudoceramide of the present invention is based on biomimetics using serinol instead of sphingosine (phytosphingosine) in the biosynthetic pathway of natural ceramides.

According to the method of the present invention, serinol as a starting material is allowed to react with an unsaturated fatty acid, for example, oleic acid, linoleic acid or linolenic acid. When the unsaturated fatty acid is oleic acid, the final product is N-(1,3-dihydroxypropan-2-yl)oleamide. When the unsaturated fatty acid is linoleic acid, the final product is (9Z,12Z)—N-(1,3-dihydroxypropan-2-yl)octadeca-9,12-dienamide. When the unsaturated fatty acid is linolenic acid, the final product is (9Z,12Z,15Z)—N-(1,3-dihydroxypropan-2-yl)octadeca-9,12,15-trienamide. Details of the preparation of the final products can be understood with reference to Scheme 1:

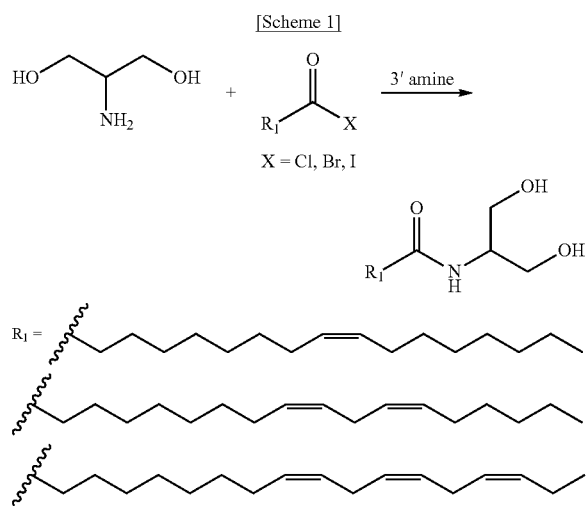

The unsaturated fatty acid may be, for example, myristoleic acid, palmitoleic acid, sapienic acid, oleic acid, elaidic acid, vaccenic acid, linoleic acid, linoelaidic acid, linolenic acid, arachidonic acid, eicosapentaenoic acid, erucic acid or docosahexaenoic acid.

Unsaturated fatty acids other than the unsaturated fatty acids shown in Scheme 1 can be basically prepared based on Scheme 1 because they are only different in the numbers of carbon atoms and double bonds therein.

The unsaturated fatty acid halide refers to an unsaturated fatty acid derivative prepared by replacing the —OH moiety of the carboxyl group in the corresponding unsaturated fatty acid with a halogen element. Fluorine, chlorine, bromine, iodine or astatine may be exemplified as the halogen. The unsaturated fatty acid halide can be prepared by halogenation of the corresponding unsaturated fatty acid. Synthetic methods for unsaturated fatty acid halides are well known to those skilled in the art and a detailed description thereof is thus omitted.

Another aspect of the present invention is directed to a cosmetic composition including the pseudoceramide compound as an active ingredient.

Particularly, the scope of the present invention is not limited to the synthesis of the pseudoceramide compound and the method for preparing the pseudoceramide compound and can be extended to the use of the pseudoceramide compound for cosmetic applications due to the antioxidant, anti-inflammatory, skin whitening, and skin moisturizing efficacies and effects of the pseudoceramide compound. Therefore, the present invention is of great technical significance in that the pseudoceramide compound can be used for cosmetic applications due to its antioxidant, anti-inflammatory, skin whitening, and skin moisturizing effects independently of whether it is a novel material. Further details can be found in the Examples section that follows.

As used herein, the term "antioxidant" refers to the suppression or relief of oxidative stress, the term "anti-inflammatory" refers to the suppression or reduction of the production of inflammatory substances, the term "skin whitening" refers to the suppression or reduction of the production of skin melanin pigments, and the term "skin moisturization" refers to assistance in or contribution to the maintenance of moisture in the skin.

The cosmetic composition of the present invention can be blended with one or more components well known to those skilled in the art. Examples of such components include oils and fats, humectants, emollients, surfactants, organic and inorganic pigments, organic powders, UV absorbers, preservatives, bactericides, antioxidants, plant extracts, pH adjusting agents, alcohols, dyes, perfumes, blood circulation promoters, cold sensation-imparting agents, antiperspirants, purified water, and vitamins (particularly, vitamin C and tocopherol).

The cosmetic composition of the present invention may take the form of a solution, emulsion or viscous mixture. The cosmetic composition of the present invention can be prepared into formulations known in the art, for example, emulsions, creams, lotions, packs, foundations, essences, and hair cosmetics.

Mode for Carrying Out the Invention

The present invention will be explained in more detail with reference to the following examples, including experimental examples. However, it is noted that these examples are not intended to limit the scope of the present invention.

EXAMPLES

Example 1: Preparation of N-(1,3-dihydroxypropan-2-yl)oleamide

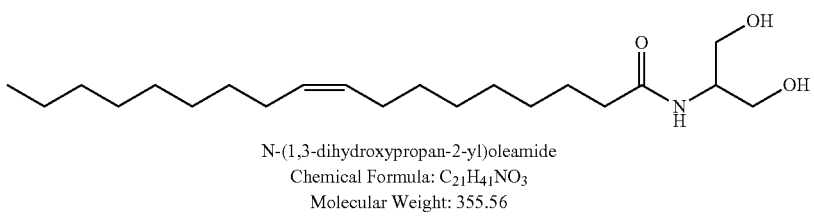 [SMILES: CCCCCCCC/C=C\CCCCCCCC(=O)NC(CO)CO]

N-(1,3-dihydroxypropan-2-yl)oleamide
Chemical Formula: $C_{21}H_{41}NO_3$
Molecular Weight: 355.56

25.51 g of serinol and 47 ml of triethylamine were placed in a reaction flask, and 100 ml of ethanol and 250 ml of dichloromethane were added thereto. Then, the temperature was reduced to ~5° C. A solution of 104 ml of oleyl chloride and 100 ml of dichloromethane were added dropwise to the reaction flask. The resulting solution was stirred at room temperature for 6 h. The reaction solution was concentrated under reduced pressure. The concentrate was dissolved in 500 ml of dichloromethane and washed with a 0.5 N aqueous hydrochloric acid solution, a saturated aqueous sodium bicarbonate solution, and water. The organic layer was dried over anhydrous magnesium sulfate, filtered, concentrated under reduced pressure to remove the organic solvents, and recrystallized to give 83 g (yield 83%) of the title product as a light yellow solid.

$^1$H NMR (400 MHz, DMSO-d$_6$) δ 7.41 (d, J=8 Hz, 1H), 5.34-5.31 (m, 2H), 4.57-4.54 (m, 2H), 3.71-3.67 (m, 1H), 3.39-3.36 (m, 4H), 2.06 (t, J=7.4 Hz, 2H), 1.99-1.98 (m, 4H), 1.48-1.45 (m, 2H), 1.29-1.24 (m, 20H), 0.86 (t, J=6.2 Hz, 3H); $^{13}$C NMR (100 MHz, CDCl$_3$) δ 172.03, 129.60, 60.19, 52.70, 40.13, 35.39, 31.25, 29.10, 29.06, 28.80, 28.68, 28.65, 28.55, 26.59, 26.54, 25.30, 22.06, 13.92; FT-IR (Neat) 3301 cm$^{-1}$, 2925 cm$^{-1}$, 2852 cm$^{-1}$, 1641 cm$^{-1}$, 1549 cm$^{-1}$, 1468 cm$^{-1}$, 1386 cm$^{-1}$, 1248 cm$^{-1}$, 1073 cm$^{-1}$, 1059 cm$^{-1}$; MS(ESI): m/z=378.30 [M+Na]$^+$.

Example 2: Preparation of (9Z,12Z)—N-(1,3-dihydroxypropan-2-yl)octadeca-9,12-dienamide

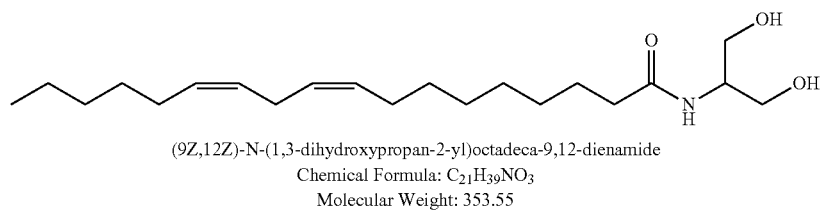 [SMILES: CCCCC/C=C\C/C=C\CCCCCCCC(=O)NC(CO)CO]

(9Z,12Z)-N-(1,3-dihydroxypropan-2-yl)octadeca-9,12-dienamide
Chemical Formula: C$_{21}$H$_{39}$NO$_3$
Molecular Weight: 353.55

0.9 g of serinol and 2 ml of triethylamine were placed in a reaction flask, and 3 ml of methanol and 20 ml of dichloromethane were added thereto. Then, the temperature was reduced to ~5° C. A solution of 3.0 g of linoleoyl chloride and 20 ml of dichloromethane were added dropwise to the reaction flask. The resulting solution was stirred at room temperature for 6 h. The reaction solution was concentrated under reduced pressure. The concentrate was dissolved in 30 ml of dichloromethane and washed with a 0.5 N aqueous hydrochloric acid solution, a saturated aqueous sodium bicarbonate solution, and water. The organic layer was dried over anhydrous magnesium sulfate, filtered, concentrated under reduced pressure, and recrystallized to give 2.8 g (yield 80%) of the title product as a light yellow solid.

$^1$H NMR (400 MHz, DMSO-d$_6$) δ 7.41 (d, J=8 Hz, 1H), 5.36-5.30 (m, 4H), 4.57-4.54 (m, 2H), 3.70-3.68 (m, 1H), 3.39-3.37 (m, 4H), 2.74 (t, J=6.2 Hz, 2H), 2.08-1.99 (m, 6H), 1.48-1.45 (m, 2H), 1.32-1.25 (m, 16H), 0.88-0.86 (m, 3H); $^{13}$C NMR (100 MHz, CDCl$_3$) δ 172.03, 129.70, 127.71, 60.19, 52.70, 40.13, 35.39, 30.87, 29.02, 28.70, 28.64, 28.58, 26.62, 26.58, 25.31, 25.18, 21.94, 13.89; FT-IR (Neat) 3301 cm$^{-1}$, 2927 cm$^{-1}$, 2853 cm$^{-1}$, 1641 cm$^{-1}$, 1548 cm$^{-1}$, 1467 cm$^{-1}$, 1073 cm$^{-1}$, 1058 cm$^{-1}$; MS(ESI): m/z=376.28 [M+Na]$^+$.

Example 3: Preparation of (9Z,12Z,15Z)—N-(1,3-dihydroxypropan-2-yl)octadeca-9,12,15-trienamide 0.9 g of serinol and 2 ml of triethylamine were placed in a reaction flask, and 3 ml of methanol and 20 ml of dichloromethane were added thereto. Then, the temperature was reduced to ~5° C. A solution of 3.0 g of α-linoleoyl chloride and 20 ml of dichloromethane were added dropwise to the reaction flask. The resulting solution was stirred at room temperature for 6 h. The reaction solution was concentrated under reduced pressure. The concentrate was dissolved in 30 ml of dichloromethane and washed with a 0.5 N aqueous hydrochloric acid solution, a saturated aqueous sodium bicarbonate solution, and water. The organic layer was dried over anhydrous magnesium sulfate, filtered, concentrated under reduced pressure, and recrystallized to give 2.9 g (yield 82%) of the title product as a light yellow solid.

$^1$H NMR (400 MHz, DMSO-d$_6$) δ 7.41 (d, J=8 Hz, 1H), 5.36-5.30 (m, 6H), 4.57-4.54 (m, 2H), 3.70-3.69 (m, 1H), 3.38-3.32 (m, 4H), 2.79-2.37 (m, 4H), 2.08-2.02 (m, 6H), 1.48-1.45 (m, 2H), 1.30-1.26 (m, 6H), 0.93 (t, J=7.6 Hz, 3H); $^{13}$C NMR (100 MHz, CDCl$_3$) δ 172.53, 131.95, 130.37, 130.19, 128.39, 128.38, 128.20, 128.00, 127.44, 60.67, 53.18, 35.88, 31.36, 29.51, 29.18, 29.14, 29.06, 27.11, 27.06, 25.79, 25.66, 25.57, 22.44, 20.50, 14.58, 14.39; FT-IR (Neat) 3300 cm$^{-1}$, 2928 cm$^{-1}$, 2853 cm$^{-1}$, 1641 cm$^{-1}$, 1548 cm$^{-1}$, 1467 cm$^{-1}$, 1424 cm$^{-1}$, 1387 cm$^{-1}$, 1248 cm$^{-1}$, 1073 cm$^{-1}$, 1058 cm$^{-1}$; MS(ESI): m/z=374.27 [M+Na]$^+$.

Examples 4 to 6—Preparation of Cosmetic Compositions

Cosmetic compositions were prepared as shown in Table 1. Each of the pseudoceramides of Examples 1-3 was uniformly dissolved throughout the corresponding composition and caused no problems when formulated.

TABLE 1

| Components | Comparative Example 1 | Example 4 | Example 5 | Example 6 |
|---|---|---|---|---|
| Example 1 | — | 0.25 | — | — |
| Example 2 | — | — | 0.25 | — |
| Example 3 | — | — | — | 0.25 |
| Butylene glycol | 20.00 | 20.00 | 20.00 | 20.00 |

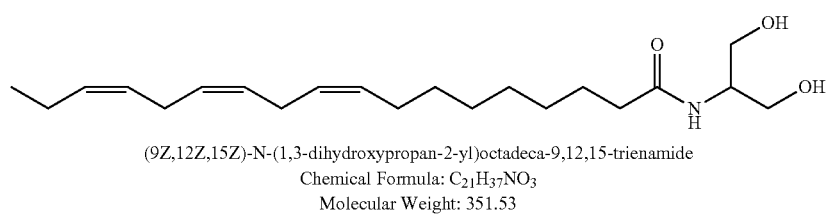 [SMILES: CC/C=C\C/C=C\C/C=C\CCCCCCCC(=O)NC(CO)CO]

(9Z,12Z,15Z)-N-(1,3-dihydroxypropan-2-yl)octadeca-9,12,15-trienamide
Chemical Formula: C$_{21}$H$_{37}$NO$_3$
Molecular Weight: 351.53

TABLE 1-continued

| Components | Comparative Example 1 | Example 4 | Example 5 | Example 6 |
|---|---|---|---|---|
| Glyceryl stearate | 4.44 | 4.44 | 4.44 | 4.44 |
| Dicaprylyl carbonate | 4.44 | 4.44 | 4.44 | 4.44 |
| Cocoglycerides | 4.44 | 4.44 | 4.44 | 4.44 |
| Glycerin | 2.67 | 2.67 | 2.67 | 2.67 |
| 1,2-hexanediol | 1.07 | 1.07 | 1.07 | 1.07 |
| Cetearyl alcohol | 0.89 | 0.89 | 0.89 | 0.89 |
| Phenoxyethanol | 0.27 | 0.27 | 0.27 | 0.27 |
| Tocopheryl acetate | 0.09 | 0.09 | 0.09 | 0.09 |
| Sodium polyacrylate | 0.09 | 0.09 | 0.09 | 0.09 |
| Water | To 100 | | | |

EXPERIMENTAL EXAMPLES

Experimental Example 1: Evaluation of Inhibitory Activities of the Pseudoceramide Compounds on Nitric Oxide (NO) Production The inhibitory activities of the pseudoceramide compounds of Examples 1-3 on nitric oxide (NO) production induced by lipopolysaccharide (LPS) in macrophage cells were investigated. 2-Amino-4-methylpyridine (10 μM) was used as a positive control. First, NO synthase was expressed in LPS-treated RAW 264.7 macrophage cells and the quantity of NO produced was measured by the Griess method. Griess reagent (1% sulfanylamine, 0.1% N-(1-naphthyl)-ethylenediamine dihydrochloride, 2.5% $H_3PO_4$) oxidizes NO to $NO_2$. The $NO_2$ concentration was determined from a calibration curve of $NaNO_2$ by measuring the absorbance at 540 nm. Specifically, RAW 264.7 macrophage cells were cultured in DMEM medium until a density of $1 \times 10^5$ cells/ml was reached. Cells were plated in 48 wells and cultured for 18 h. After cells were adherent to the wells, 20 μl of LPS (1 m/ml) and 100 μl of each of the samples, including 2-amino-4-methylpyridine as a positive control, were added to each well. Cells were cultured for 20 h and the quantity of NO produced in the culture was determined using Griess reagent.

The results are shown in Table 2 and FIG. 1.

TABLE 2

| | | Cell viability (%) |
|---|---|---|
| Example 1 | 5.0 | 100.99 |
| | 10.0 | 102.08 |
| | 25.0 | 102.14 |
| | 50.0 | 102.22 |
| Example 2 | 5.0 | 100.35 |
| | 10.0 | 100.24 |
| | 25.0 | 100.09 |
| | 50.0 | 93.80 |
| Example 3 | 5.0 | 95.72 |
| | 10.0 | 101.01 |
| | 25.0 | 96.58 |
| | 50.0 | 96.64 |
| 2-Amino-4-methylpyridine | 10 μM | 103.13 |

The cell viabilities of Raw264.7 macrophage cells were assessed by MTT assay to evaluate the cytotoxicities of the pseudoceramide compounds. When the cell viability was ≥80% by MTT assay, the pseudoceramide compound was judged to be not cytotoxic. The cell viabilities of the pseudoceramide compounds were ≥95% at concentrations of 1-50 μg/mL, indicating no toxicity to Raw264.7 macrophage (Table 1). Another experiment for anti-inflammatory effects of the pseudoceramide compounds was conducted at concentrations of 1-50 μg/mL.

As can be seen from the results in Table 2 and FIG. 1, the inhibitory activity of each of the compounds of Examples 1-3 on NO production was lower than that of the positive control 2-amino-4-methylpyridine but increased in a concentration-dependent manner.

Experimental Example 2: Evaluation of Inhibitory Activities of the Pseudoceramide Compounds on Inflammatory Cytokine Production The inhibitory activities of the pseudoceramide compounds of Examples 1-3 on IL-6 and $PGE_2$ production induced by lipopolysaccharide (LPS) in macrophage cells were investigated. Dexamethasone (10 μM) was used as a positive control.

IL-6 and $PGE_2$ are produced by several intracellular signaling systems activated by irritants such as lipopolysaccharide (LPS) in macrophage cells. When overproduced, IL-6 and $PGE_2$ cause inflammatory responses. The anti-inflammatory activities of the pseudoceramide compounds can be determined by inhibiting the overproduction of IL-6 and $PGE_2$ by LPS. Raw264.7 macrophage cells were plated in a 24-well plate at a density of $3 \times 10^5$ cells/well and cultured for 24 h. Thereafter, cells were treated with different concentrations of the samples and cultured for 1 h. Each well was treated with LPS at a concentration of 1 μg/ml. After 24-h culture, the supernatant was collected and the quantities of IL-6 and $PGE_2$ produced in the supernatant were measured.

Figure 2:
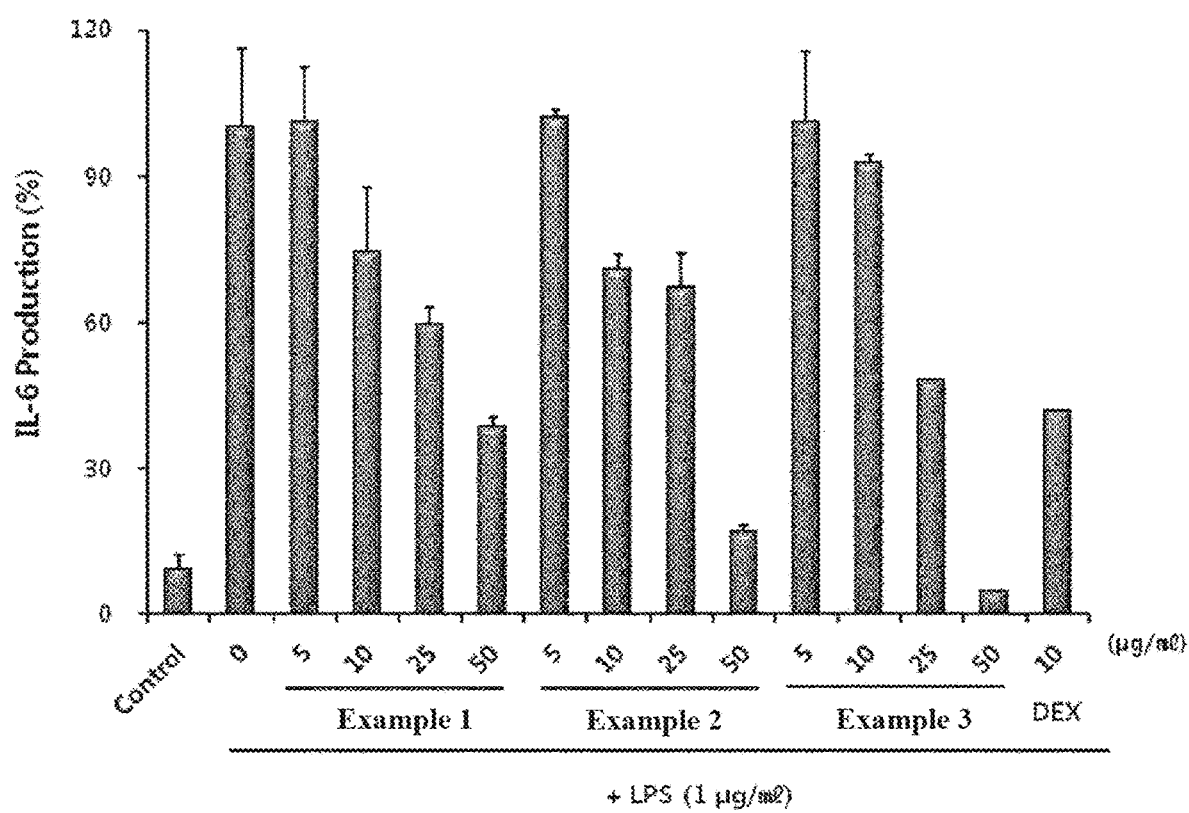
FIG. 2 is a graph showing the inhibitory activities of pseudoceramide compounds prepared in Examples 1-3 on IL-6 production.
Figure 3:
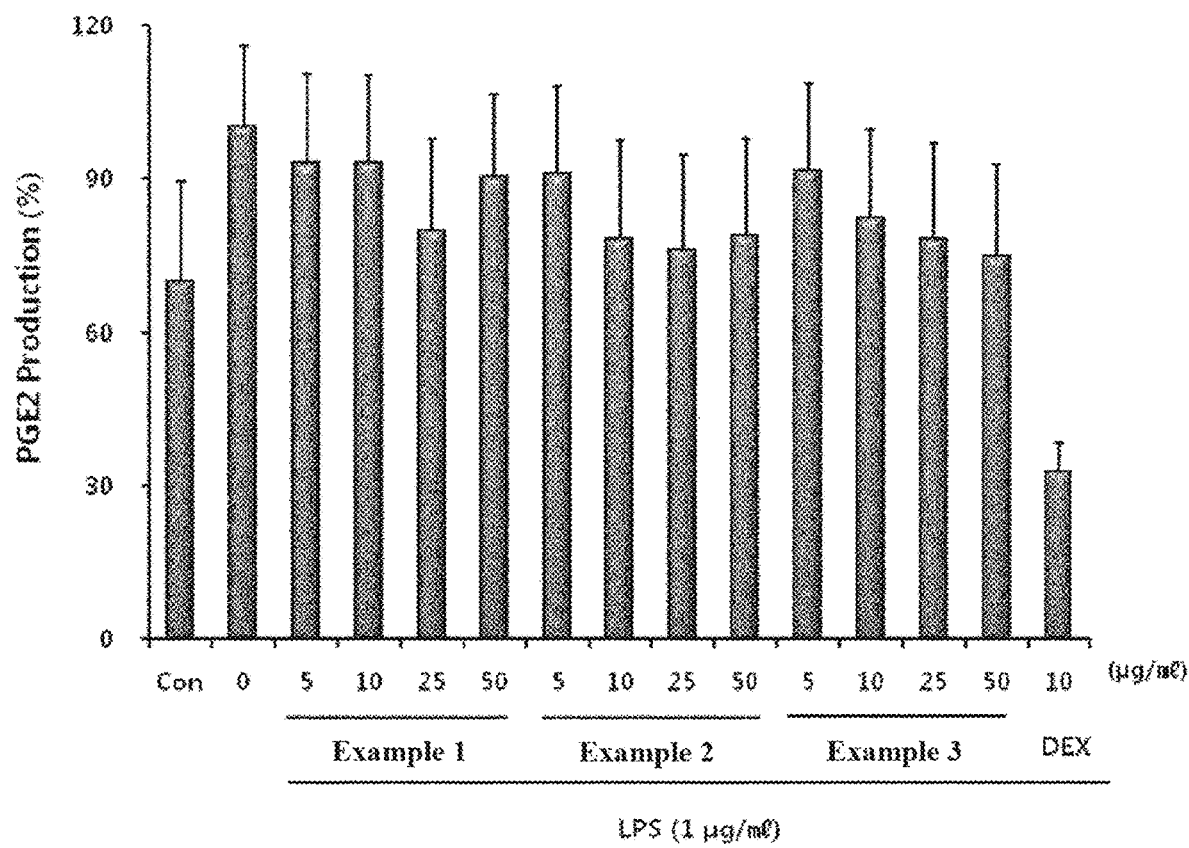
FIG. 3 is a graph showing the inhibitory activities of pseudoceramide compounds prepared in Examples 1-3 on $PGE_2$ production.

The results are shown in FIGS. 2 and 3.

As can be seen from the results in FIGS. 2 and 3, the compounds of Examples 1-3 showed similar activities to the positive control Dexamethasone and concentration-dependent inhibitory activities on IL-6 and $PGE_2$ production.

Experimental Example 3: Inhibitory Effects of the Pseudoceramide Compounds on Melanin Production The inhibitory effects of the compounds of Examples 1-3 on melanin production in cells were investigated (Chang and Chen, 2012).

For a cell experiment, fetal bovine serum (FBS) and Dulbecco's modified Eagle medium (DMEM) were purchased from Gibco (USA) and mouse-derived B16F10 melanoma cells were purchased from the Korean Cell Line Bank. Cells were cultured in DMEM medium (Gibco) supplemented with 10% FBS (Gibco) and 1% antibiotic-antimycotic (Gibco) in a 5% $CO_2$ incubator at 37° C. Cells were passaged every 3-4 days. Cultured B16F10 cells were detached with 0.05% trypsin-EDTA. 24 h after cells were inoculated into a 24-well plate at the same density ($2.0 \times 10^4$ cells/well), cells were treated with α-MSH (100 nM) and each test drug and cultured for 3 days. Cells were treated with 1 N NaOH and allowed to react for 1 h to dissolve out melanin therefrom. The absorbance was measured at 405 nm to determine the quantity of melanin. Arbutin (500 ppm) was used as a positive control. The results are shown in FIGS. 4 and 5.

Figure 4:
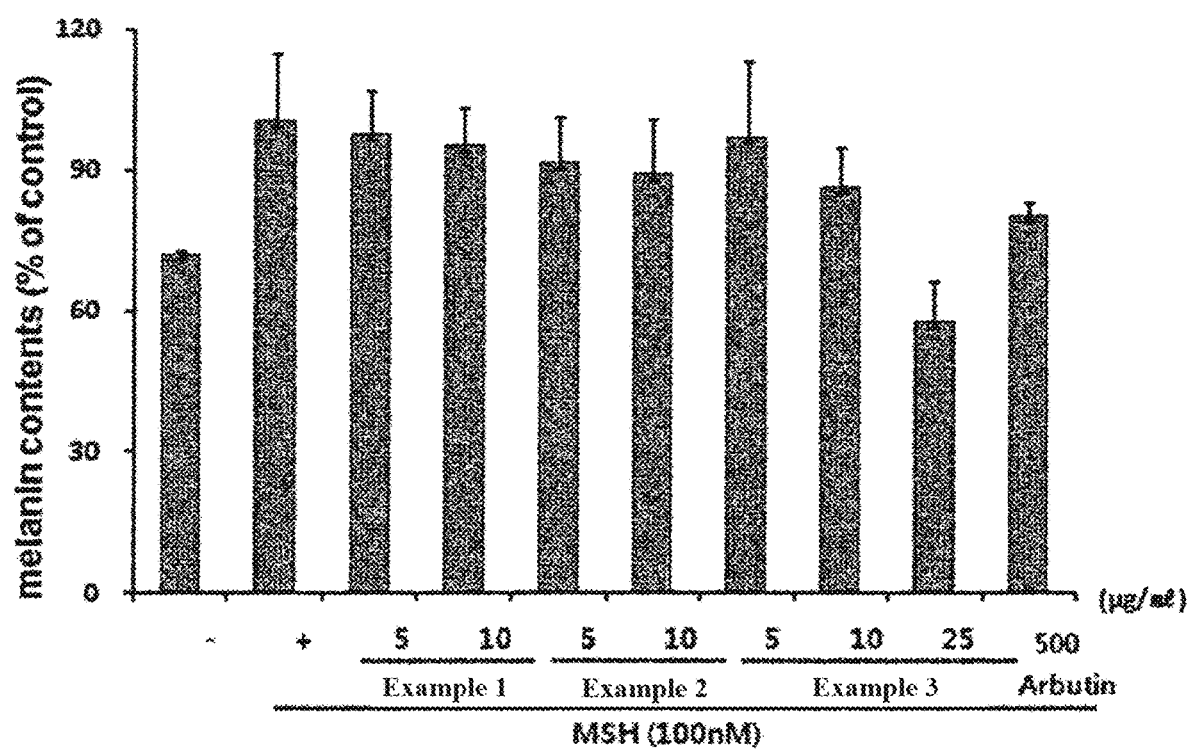
FIG. 4 is a graph showing the inhibitory activities of pseudoceramide compounds prepared in Examples 1-3 on melanin production.
Figure 5:
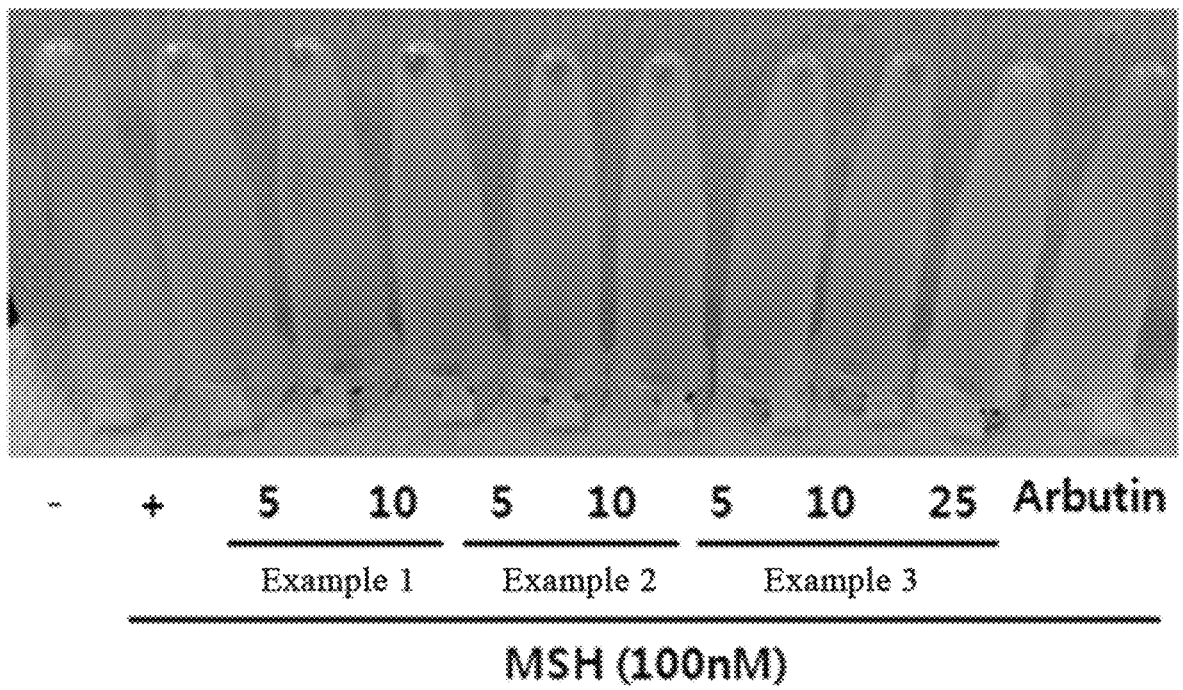
FIG. 5 shows images of experimental and control groups used to investigate the inhibitory effects of pseudoceramide compounds prepared in Examples 1-3 on melanin production.

As can be seen from the results of FIGS. 4 and 5, the activities of the compounds of Examples 1-3 were similar to or higher than that of the positive control arbutin at low concentrations. The compounds of Examples 1-3 showed concentration-dependent inhibitory activities on melanin production.

Experimental Example 4: Increased Ability of the Pseudoceramide Compounds to Moisturize the Human Skin The abilities of the lotions prepared in Examples 4-6 and Comparative Example 1 to moisturize the skin were compared. Before and 30 min, 1 h, and 3 h after application of each lotion, the skin moisture contents of 23 male and female adults in their 20-50s were measured using a Corneometer (Cutometer®, dual MPA580, Germany) under constant temperature and constant humidity conditions (24° C., 40-50% RH). A probe was attached to the skin surface and the moisture content of the surface site was measured. For higher reliability, the measurement was repeated three times and the measured values were averaged. A higher value indicates the presence of a larger amount of moisture.

The results are shown in Table 3.

TABLE 3

| | Skin moisture content before application (average) | Skin moisture content after application (average) | |
|---|---|---|---|
| | | 1 h after application | 3 h after application |
| Comparative Example 1 | 28.9 | 43.9 | 41.8 |
| Example 4 | 28.9 | 61.2 | 54.5 |
| Example 5 | 28.9 | 60.1 | 57.4 |
| Example 6 | 28.9 | 59.3 | 57.3 |

The electrical properties of the stratum corneum vary when hydrated. The dry stratum corneum has low electrical conductivity, and hydration increases the dielectric constant of the stratum corneum, resulting in high electrical conductivity. Based on the fact that the skin moisture is proportional to the capacitance of the skin, higher electrical conductivities of the skin were achieved after application of each of the lotions of Examples 4-6 than before application and after application of the lotion of Comparative Example 1 (see Table 3), demonstrating that the pseudoceramide compounds of Examples 1-3 are very effective in moisturizing the skin.

Experimental Example 5: Increased Sebum Content of the Skin

Increases in sebum content after application of the lotions of Examples 4-6 and Comparative Example 1 were compared.

The serum contents of the skin were measured using a Sebumeter®SM815 (Cutometer®, dual MPA580, Germany). Specifically, a probe attached with a translucent lipid-absorbing tape was slightly pressed against the skin surface for 30 sec such that the lipid-absorbing tape was brought into contact with the skin surface, and as a result, sebum was adsorbed to the lipid-absorbing tape. Thereafter, the probe was pushed down against the sebumeter and its transmittance was measured based on the photometric reflection. The measurement was performed once for the skin surface. The sebum content was expressed in $\mu g/cm^2$.

The results are shown in Table 4.

TABLE 4

| | Sebum content of the skin after application (average) | |
|---|---|---|
| | 1 h after application | 3 h after application |
| Comparative Example 1 | 68.6 | 44.3 |
| Example 4 | 151.7 | 95.7 |
| Example 5 | 165.5 | 91.1 |
| Example 6 | 149.3 | 73.2 |

The sebum contents of the skin were higher overall when the lotions of Examples 4-6 were applied than when the lotion of Comparative Example 1 was applied, indicating that the pseudoceramide compounds of Examples 1-3 assist in moisturizing the skin. The ability of the lotion of Example 6 to moisturize the skin was similar to those of the lotions of Examples 4 and 5, while the sebum content of the skin after application of the lotion of Example 6 was relatively low compared to those after application of the lotions of Examples 4 and 5.

The invention claimed is:

1. A cosmetic composition comprising the pseudoceramide compound represented by Formula 2 in a concentration of 25–50 µg/mL:

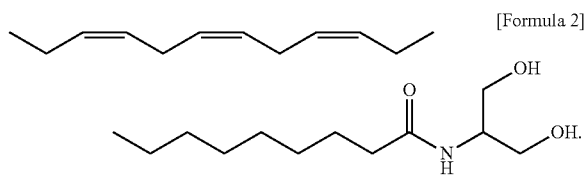

[Formula 2]